United States Patent [19]

Appel et al.

[11] Patent Number: 4,782,189

[45] Date of Patent: Nov. 1, 1988

[54] PROCESS FOR THE CONTINUOUS PREPARATION OF LAUROYL PEROXIDE

[75] Inventors: Hans Appel; Gottfried Brossmann, both of Höllriegelskreuth, Fed. Rep. of Germany

[73] Assignee: Peroxid-Chemie GmbH, Hollriegelskreuth, Fed. Rep. of Germany

[21] Appl. No.: 96,851

[22] Filed: Sep. 15, 1987

Related U.S. Application Data

[63] Continuation of Ser. No. 691,720, Jan. 15, 1985, abandoned, which is a continuation of Ser. No. 166,280, Jul. 7, 1980, abandoned.

[30] Foreign Application Priority Data

Jul. 11, 1979 [DE] Fed. Rep. of Germany ....... 2928020

[51] Int. Cl.$^4$ ........................................... C07C 178/00
[52] U.S. Cl. ..................................................... 568/566
[58] Field of Search ........................................ 568/566

[56] References Cited

U.S. PATENT DOCUMENTS 2,771,492  11/1956  Chapman et al. .................. 568/566

Primary Examiner—Alan L. Rotman
Assistant Examiner—Robert C. Whittenbaugh
Attorney, Agent, or Firm—Felfe & Lynch

[57] ABSTRACT

The invention provides an improvement for the continuous preparation of lauroyl peroxide in the absence of organic solvents from crude lauroyl chloride, aqueous sodium hydroxide solution and hydrogen peroxide by continuously adding the reaction components to a reaction stirrer vessel and carrying out the reaction with an average residence time of 15 to 30 minutes, the improvement comprising maintaining the temperature in the raction vessel between 0° and 20° C. by cooling, adding 1.0 to 3% by weight of hydrogen peroxide, referred to the total amount of the reaction mixture, and sodium hydroxide in such amount that the concentration thereof in the reaction mixture run off is 0.15 to 0.30N, withdrawing the reaction mixture from the reaction vessel and heating the reaction mixture by the addition of water of a temperature of from 70° to 90° C., to above the melting point of lauroyl peroxide, and separating off the molten lauroyl peroxide in a separator.

13 Claims, No Drawings

PROCESS FOR THE CONTINUOUS PREPARATION OF LAUROYL PEROXIDE

This is a continuation of application Ser. No. 691,720 filed on Jan. 15, 1985, abandoned which is a continuation of application Ser. No. 166,280 filed on July 7, 1980, now abandoned.

The present invention is concerned with a process for the continuous preparation of lauroyl peroxide.

Lauroyl peroxide, the systematic chemical name of which is dilauroyl peroxide, is a much used catalyst for polymerization reactions. It is prepared by reacting lauroyl chloride with hydrogen peroxide under varying conditions of temperature, time and pH. In essence, there are two types of processes: first, those in which the acid chloride is reacted in an organic solvent, especially in petroleum ether (benzine) and, secondly, those which do not use an organic solvent. The processes using an organic solvent can be carried out at a relatively low temperature. This is of advantage since, under these conditions, in spite of relatively long reaction times, the decomposition of hydrogen peroxide and organic peroxide and the hydrolysis of the acid chloride only take place slowly. The processes carried out without the use of organic solvents, on the other hand, operate at temperatures above the melting point of lauroyl peroxide, i.e. from 50° to 70° C., and employ very short reaction or residence times (see Federal Republic of Germany Pat. No. 1,643,599 and German Democratic Republic Pat. No. 38,072).

An important disadvantage of processes carried out with the use of organic solvents is that it is practically impossible to recover these solvents and this gives rise to considerable problems with regard to the contamination of exhaust air. Furthermore, the treatment of the waste water from the processes gives rise to considerable problems. In spite of flotation and treatment of the flotation sludge, the waste water loading remains high. On the other hand, in the case of processes operating without the use of organic solvents, the high reaction temperatures used are disadvantageous since, as a result of the short residence times, the control of the reaction is difficult and the handling of the decomposable peroxide at these high temperatures makes special precautionary measures necessary.

It is, therefore, an object of the present invention to overcome the disadvantages of these two types of processes and to provide a continuous process for the preparation of lauroyl peroxide which, on the one hand, does not require the use of organic solvents and, on the other hand, can be carried out at just as low or even lower temperatures, like the processes making use of solvents.

Thus, according to the present invention, there is provided a process for the continuous preparation of lauroyl peroxide in the absence of organic solvents from crude lauroyl chloride, aqueous sodium hydroxide solution and hydrogen peroxide by continuously adding the reaction components to a stirred reaction vessel and carrying out the reaction with an average residence time of 15 to 30 minutes, wherein the temperature in the reaction vessel is maintained by cooling at from 0° to 20° C., wherein 1.0 to 3% by weight of hydrogen peroxide, referred to the total amount of the reaction batch, and sodium hydroxide in such an amount that the concentration thereof in the reaction mixture running off is from 0.15 to 0.30N are added thereto, the reaction mixture withdrawn from the reaction vessel is heated, by adding water of a temperature of from 70° to 90° C. to above the melting temperature of lauroyl peroxide and the molten lauroyl peroxide is separated off in a separator.

Surprisingly, when carrying out the process in the manner according to the present invention, it is possible, without the addition of organic solvents, significantly to lower the high reaction temperatures previously necessary in the case of solvent-free processes without hereby impairing the handlability of the solution.

The reaction temperature used is preferably from 5° to 15° C.

The quantity of sodium hydroxide added to the reaction vessel is, preferably, such that the concentration of sodium hydroxide in the reaction mixture withdrawn from the vessel is from 0,18 Normal to 0,25 Normal. Generally, the concentration of sodium hydroxide in the reaction vessel itself is not critical; it is the concentration in the reaction mixture withdrawn from the vessel which matters.

The acid chloride used is preferably a product such as is obtainable by the chlorination of lauric acid with phosphorous trichloride, the crude chloride thus obtained preferably being used without further purification. It is preferred to use a crude chloride with a saponifiable chloride content of 101 to 110%, referred to pure lauroyl chloride.

The average residence time under the above-given preferred reaction conditions is 20 to 25 minutes. A reduction of the reaction time is possible but the chloride content of the product then increases.

The hydrogen peroxide concentration in the aqueous reaction phase is preferably 1.5 to 2.5% by weight. In the case of higher concentrations, an increasing amount of foam formation occurs. It is preferable to use an excess.

The amount of hydrogen peroxide used in excess of the theoretically necessary amount is preferably 30 to 60%. A lowering of the excess increases the chlorine content in the product. The excess amount can easily be determined in the run-off.

The sodium hydroxide concentration is especially critical within the scope of the present invention. It is controlled according to the alkalinity of the mother liquor running off. The sodium hydroxide is preferably used in a concentration equivalent to the amount of hydrogen peroxide, i.e. in an excess of 30 to 60% over the amount theoretically necessary. Apart from by the amount of added sodium hydroxide, its concentration can also be finely regulated in the run-off by the dilution of the reaction mixture with water.

If the sodium hydroxide concentration in the run-off exceeds the admissible upper concentration limit, then foam formation occurs and the content of per acid in the waste acid increases. Going below the given concentration leads to an increase of the chloride content of the product. Furthermore, the active oxygen content in the product then also decreases.

The continuous reaction is preferably started up batchwise, dosing in of the reaction components being commenced as soon as the concentration values given for the run-off are achieved in the reaction vessel.

The withdrawn reaction mixture is heated with water of a temperature of 70° to 90° C. to above the melting point of lauroyl peroxide and preferably to a temperature of from 56° to 65° C. The molten lauroyl peroxide can then be directly separated off in a separator. The volume of water necessary for this purpose is generally 1.5 to 3 times the volume of run-off. This means that the reaction mixture running off is mixed in a volume ratio of 1:1.5 to 1:3 with hot water with the given temperature. According to a preferred embodiment of the process according to the present invention, the pH value is thereby simultaneously reduced by the addition of an acid and preferably of a mineral acid, for example sulphuric acid or phosphoric acid, to a value of from 9.5 to 11. A reduction below pH 9.5 should be avoided since otherwise lauric acid will be liberated.

According to a further preferred embodiment of the process according to the present invention, a heavy metal salt is also preferably added to the reaction solution running off. Especially good results are achieved with divalent iron salts, such as ferrous sulphate. This embodiment of the process according to the present invention leads to an improved purity of the product and especially to a reduction of the active oxygen content in the waste acid. However, instead of iron salts, other heavy metal salts, for example, manganese, nickel or chromium salts, can also be used. When using iron salts, the addition of from 0.001 to 0.05% by weight of iron ions/kg. lauroyl peroxide has proved to be favourable. This corresponds, in the case of using ordinary ferrous sulphate containing water of crystallization, to about 50 mg./kg. lauroyl peroxide. Furthermore, the heavy metal salt suppresses a possible foam formation in the separator.

The achieved reduction of the active oxygen content in the lauric acid recovered as waste product makes it possible to recover the lauric acid in pure form by distillation, without danger.

The mother liquor separated off in the separator is acidified and separated in a further separator into waste acid and waste water. The waste water runs off almost uncontaminated and can, after neutralization, be passed into the main drains without special further measures.

The following Example is given for the purpose of illustrating the present invention:

EXAMPLE

Into an open stirred vessel of stainless steel equipped with a cooling jacket, cooling coil, high speedstirrer and overflow pipe, there are continuously introduced, per hour, 13.95 g. crude lauroyl chloride (about 102 to 106% saponifiable chlorine), as well as aqueous sodium hydroxide solution and hydrogen peroxide in such amounts that the sodium hydroxide concentration in the run-off is 0.2N and the amount of hydrogen peroxide in the run-off is 0.6%. The residence time in the vessel is from 20 to 25 minutes at a temperature of from 10° to 15° C., which is maintained by cooling. The reaction components are introduced through inlet pipes which terminate just above the bottom of the vessel. The reaction mixture running off through the overflow is diluted with an equal amount of water at ambient temperature, the pH value is reduced to 10.5 to 11 with concentrated sulphuric acid and the reaction mixture is mixed with 50 mg. ferrous sulphate heptahydrate/kg. lauroyl peroxide in the solution and then heated to 56° to 60° C. with a 1.5 fold amount of water with a temperature of about 85° C. The mixture so obtained is directly separated in a separator. The mother liquor running off from the separator is adjusted, in a stirrer vessel, with sulphuric acid to a pH of 1 to 2 and passed through another separator in which waste acid and waste water are separated. There are thus obtained about 11.9 kg./hour of lauroyl peroxide and 0.5 kg./hour of waste acid.

It will be understood that the specification and examples are illustrative, but not limitative of the present invention and that other embodiments within the spirit and scope of the invention will suggest themselves to those skilled in the art.

What is claimed is:

1. In a process for the continuous preparation of lauroyl peroxide in the absence of organic solvents from crude lauroyl chloride, aqueous sodium hydroxide solution and hydrogen peroxide by continuously adding the reaction components to a reaction stirrer vessel and carrying out the reaction with an average residence time of 15 to 30 minutes, the improvement comprising maintaining the temperature in the reaction vessel between 0° and 20° C. by cooling, adding 1.0 to 3% by weight of hydrogen peroxide, referred to the total amount of the reaction mixture, and sodium hydroxide in such amount that the concentration thereof in the reaction mixture run off is 0.15 to 0.3N, withdrawing the reaction mixture from the reaction vessel, adding sufficient acid to the reaction mixture to reduce the pH to a value of from 9.5 to 11, and then heating the reaction mixture, by the addition of water of a temperature of from 70° to 90° C. to above the melting point of lauroyl peroxide, and separating off the molten lauroyl peroxide in a separator.

2. Improvement as claimed in claim 1 wherein the temperature and the reaction vessel is maintained at 5° to 15° C.

3. Improvement as claimed in claim 1 wherein 1.5 to 2.5% by weight of hydrogen peroxide is added.

4. Improvement as claimed in claim 3 wherein the hydrogen peroxide is used in a stoichoimetric excess of 30 to 60%.

5. Improvement as claimed in claim 1 wherein the sodium hydroxide is added in an amount such that the concentration in the reaction mixture run off is 0.18 to 0.25N.

6. Improvement as claimed in claim 5 wherein the sodium hydroxide is added in a stoichiometric excess of 30 to 60%.

7. Improvement as claimed in claim 1 wherein crude lauroyl chloride is used with a saponifiable chlorine content of 101 to 110%.

8. Improvement as claimed in claim 1 wherein the average residence time in the reaction vessel is from 20 to 25 minutes.

9. Improvement as claimed in claim 1 wherein the reaction mixture withdrawn is heated to 56°–65° C. by the addition of hot water.

10. In a process for the continuous preparation of lauroyl peroxide in the absence of organic solvents from crude lauroyl chloride, aqueous sodium hydroxide solution and hydrogen peroxide by continuously adding the reaction components to a reaction stirrer vessel and carrying out the reaction with an average residence time of 15 to 30 minutes, the improvement comprising maintaining the temperature in the reaction vessel between 0° and 20° C. by cooling, adding 1.0 to 3% by weight of hydrogen peroxide, referred to the total amount of the reaction mixture, and sodium hydroxide in such amount that the concentration thereof in the reaction mixture run off is 0.15 to 0.3N, withdrawing the reaction mixture from the reaction vessel, adding a heavy transition metal salt in an amount to give 0.001 to 0.05% by weight of heavy metal ions, adding sufficient acid to the mixture withdrawn from the reaction vessel to reduce the pH to a value of from 9.5 to 11, and heating the reaction mixture by the addition of water of a temperature of from 70° to 90° C. to above the melting point of lauroyl peroxide, and separating off the molten lauroyl peroxide in a separator.

11. Improvement as claimed in claim 10 wherein the heavy metal salt if ferrous sulphate.

12. Improvement as claimed in claim 1 wherein the acid added to the withdrawn reaction mixture is sulfuric acid or phosphoric acid.

13. Improvement as claimed in claim 10 wherein the heavy metal ions are in the form of an iron salt.

* * * * *